United States Patent
Seppi (10) Patent No.: US 7,078,699 B2
(45) Date of Patent: Jul. 18, 2006

(54) IMAGING APPARATUS AND METHOD WITH EVENT SENSITIVE PHOTON DETECTION

(75) Inventor: Edward J. Seppi, Portola Valley, CA (US)

(73) Assignee: Varian Medical Systems Technologies, Inc., Palo Alto, CA (US)

( * ) Notice: Subject to any disclaimer, the term of this patent is extended or adjusted under 35 U.S.C. 154(b) by 27 days.

(21) Appl. No.: 10/438,684

(22) Filed: May 14, 2003

(65) Prior Publication Data

US 2004/0066878 A1 Apr. 8, 2004

Related U.S. Application Data

(60) Provisional application No. 60/416,021, filed on Oct. 4, 2002.

(51) Int. Cl.
*G01N 23/02* (2006.01)

(52) U.S. Cl. ...................... 250/358.1; 378/50

(58) Field of Classification Search ............. 250/358.1, 250/363.01, 363.03, 366, 367, 368, 369; 378/50, 53, 54, 56, 57
See application file for complete search history.

(56) References Cited

U.S. PATENT DOCUMENTS

| | | | | |
|---|---|---|---|---|
| 5,751,000 A | * | 5/1998 | McCroskey et al. | 250/363.03 |
| 5,774,520 A | * | 6/1998 | Bolotin | 378/50 |
| 5,869,841 A | * | 2/1999 | Smither | 250/505.1 |
| 5,900,636 A | * | 5/1999 | Nellemann et al. | 250/363.04 |
| 5,970,115 A | * | 10/1999 | Colbeth et al. | 378/62 |
| 5,986,257 A | * | 11/1999 | Harding | 250/253 |
| 6,324,258 B1 | * | 11/2001 | Beekman | 378/145 |
| 6,380,540 B1 | * | 4/2002 | Maor et al. | 250/363.04 |
| 6,583,420 B1 | * | 6/2003 | Nelson et al. | 250/397 |
| 2004/0005027 A1 | * | 1/2004 | Nafstadius | 378/65 |

OTHER PUBLICATIONS

International Search Report dated Apr. 23, 2004.

* cited by examiner

*Primary Examiner*—Otilia Gabor
(74) *Attorney, Agent, or Firm*—Bingham McCutchen LLP (57) ABSTRACT

An imaging apparatus (10) includes a photon detector (20) and an accessing circuit (44) coupled thereto. The photon detector (20) detects photons and generates signals in response thereto. The accessing circuit (44) reads out the signals from the photon detector (20) at a sufficiently high rate so that it operates in an event sensitive mode. The apparatus (10) also includes a signal processing module (15) for processing the signals and generating data regarding the images of the object. In accordance with various embodiments of the present invention, the signal processing module (15) may include a spatial resolution circuit (56), a photon energy resolution circuit (57), a temporal resolution circuit (58), or any combination thereof.

52 Claims, 6 Drawing Sheets

IMAGING APPARATUS AND METHOD WITH EVENT SENSITIVE PHOTON DETECTION

RELATED APPLICATION DATA

This application claims priority to U.S. Provisional Patent Application No. 60/416,021, filed on Oct. 4, 2002, the entire disclosure of which is expressly incorporated by reference herein.

BACKGROUND OF THE INVENTION

The present invention relates, in general, to photon detection and imaging and in one embodiment, specifically, to event sensitive photon detection in an imaging process and detection of photons produced through interactions between an incident beam and material in the object to be imaged.

Computed tomography (CT) is widely used in medical diagnosis. In a typical CT process, a radiation source emits a thin X-ray beam while rotating around a patient. X-ray image detectors positioned at the opposite side of the patient from the radiation source pick up and record data regarding absorption of the X-ray beam by various tissues and bones in the patient. A computer processes the data and generates images that assimilate multiple X-ray images into a two-dimensional cross sectional image. The CT images reveal many soft tissue structures not shown by conventional radiography. In addition, a CT image shows an entire slice of the patient's body with greater clarity compared with a conventional X-ray radiography image using the same dosage of radiation.

A conventional CT is deficient in providing detailed information regarding a small abnormal tissue, e.g., a tumor, in the patient's body. In addition, the intrinsic noise in the electronic circuits may adversely affect the image quality of a conventional CT. Increasing the intensity of the X-ray radiation may improve the signal to noise ratio of the circuits, but will also increase radiation exposure of the patient. Excessive increase in the radiation intensity may also adversely affect the resolution of the images.

Positron emission tomography (PET) detects photons generated through positron-electron annihilation of positrons from a radioactive tracer placed in the object, e.g., patient, to be imaged, and analyzes the photon energy and trajectory to generate tomographic images of the patient. Single photon emission computed tomography (SPECT) generates images by computer analysis of photon emission events from a radioactive tracer. Positron-electron annihilation may be the source of such photon emission. PET and SPECT require the detection and analysis of single photon events. Photomultipliers are generally used for single photon event detection in PET and SPECT. The low spatial resolution of the photomultipliers may adversely affect the quality of PET and SPECT images. Other constraints on the PET and SPECT image qualities include the temporal and spatial resolution and counting rate characteristics of the photomultipliers and associated circuitry.

Accordingly, it would be advantageous to have an apparatus and a method for accurately detecting photon emission events. It is also desirable to have a photon detection apparatus that has a high signal to noise ratio for generating high quality data. It is further desirable to be able to detect the photon emissions with both high spatial resolution and high temporal resolution. It would be of further advantage to be able to produce the PET and SPECT without a radioactive tracer.

SUMMARY OF THE INVENTION

In accordance with an embodiment of the present invention, a method for examining an object is provided. The method includes directing an externally generated radiation beam towards an object to generate a positron-electron annihilation process to produce photons in the object, detecting the photons, generating a signal in response to the detected photons, and determining a characteristic of the object based at least on the signal. By means of non-limiting examples, the beam may comprise a pencil-beam, a fan beam, or a cone beam. By using an externally generated radiation beam, examination of the object may be performed without using a radioactive tracer. In one embodiment, only signals associated with an energy level that is above a certain prescribed threshold are considered, thereby improving the signal to noise ratio.

The method may be used to examine animal body or non-animal objects. In one embodiment, the object is at least a portion of an animal body who is undergoing a PET scanning or a single-photon emission computed tomography (SPECT) scanning. In another embodiment, the object includes a passenger, a luggage, or a cargo. In this case, the method may be used to determine whether the object contains contraband or explosive based on the generated data. In yet another embodiment, the object includes a mineral rock. In this case, the method may be used to determine whether the object contains a diamond.

In accordance with another embodiment, a method for examining an object is provided. The method includes generating a particle in an object, detecting the particle, and generating a signal in response to the detected particle. By means of non-limiting examples, the particle may be generated by introducing a radioactive isotope into the object, or by a positron-electron annihilation process. Also by means of non-limiting examples, the particle may comprise a proton, a positron, a neutron, or an electron. The method also includes accessing the generated signal in an event sensitive mode, in which case, the signal is accessed as the signal is generated and before the signal integrates with another signal. Accessing the generated signals in an event sensitive mode allows an accurate detection of the generated particle, and improves a signal to noise ratio of an object examination system. In one embodiment, the object is at least a portion of a body of a patient who is undergoing a PET scanning or a single-photon emission computed tomography (SPECT) scanning. In another embodiment, the object includes a passenger, a luggage, or a cargo. In this case, the method may be used to determine whether the object contains contraband or explosive based on the generated data. In yet another embodiment, the object includes a mineral rock. In this case, the method may be used to determine whether the object contains a diamond.

In accordance with another embodiment, an imaging apparatus is provided. The imaging apparatus includes a conversion panel for generating a light photon in response to a radiation, and a photo detector array aligned with the conversion panel and configured to generate a signal in response to the light photon received from the conversion panel. The imaging apparatus also includes an access circuit coupled to the photo detector array. The access circuit operates in an event sensitive mode, and reads the signal as the signal is generated and before the signal integrates with another signal. Accessing the signals in an event sensitive mode allows an accurate detection of the radiation, and improves a signal to noise ratio of the imaging apparatus.

Systems for performing PET and systems for examining an object are also provided. Other aspects and features of the invention will be evident from reading the following detailed description of the preferred embodiments, which are intended to illustrate, not limit, the invention.

DETAILED DESCRIPTION OF VARIOUS EMBODIMENTS

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

Figure 1:
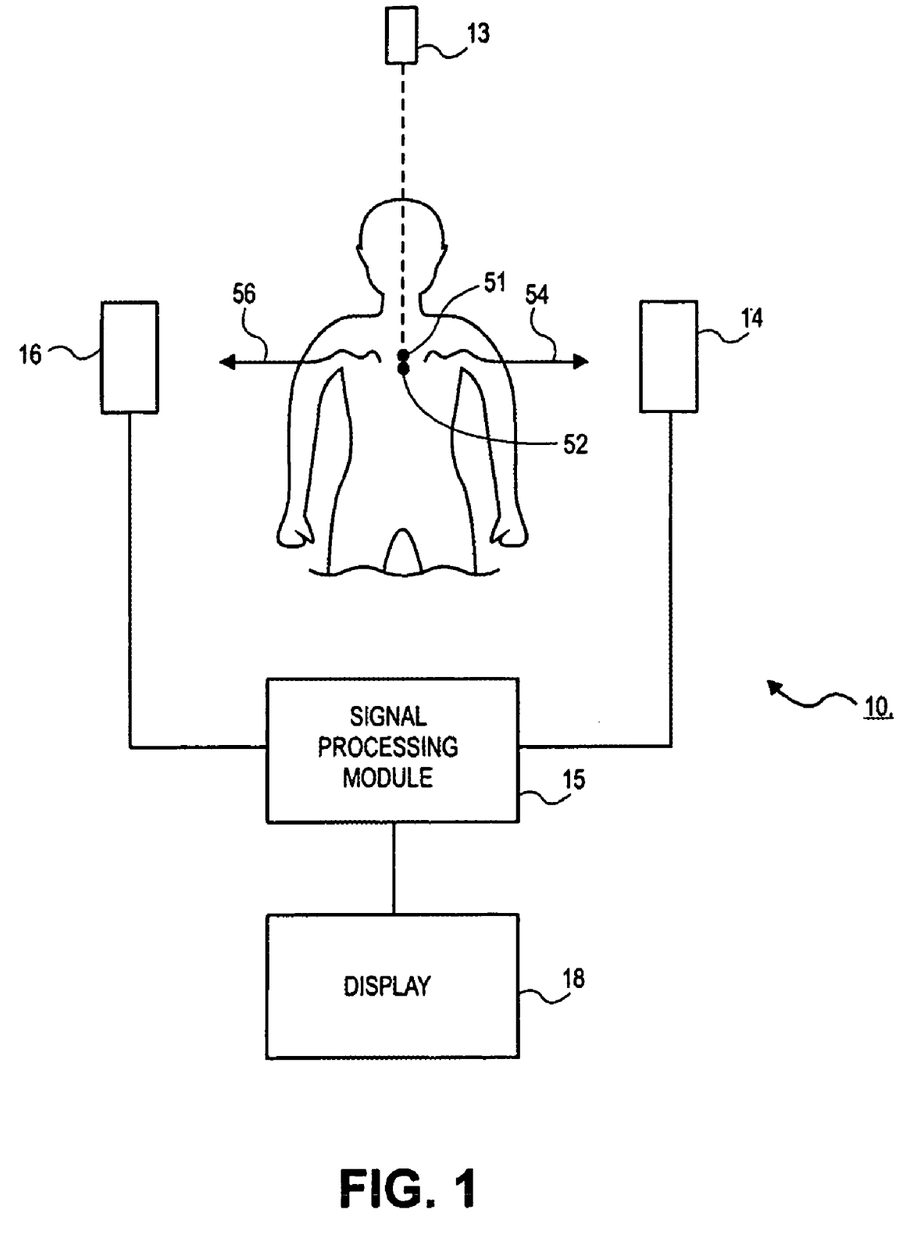
FIG. 1 is a functional block diagram illustrating a PET apparatus in accordance with one embodiment of the present invention.

FIG. 1 is a functional block diagram illustrating a positron emission tomography (PET) apparatus 10 in accordance with an embodiment of the present invention. A PET process generates images of an object, such as tissues in a patient 11, by detecting photons emitted from positron-electron annihilation in patient 11. In accordance with one embodiment, the positrons are generated from the decay of a positron-emitting radioactive isotope incorporated in a biochemical substance administrated to patient 11. Examples of biochemical substances that can be administrated to patient 11 include saline, glucose, fatty acids, etc. A biochemical substance can be administrated to patient 11 through intravenous injection, oral intake, implantation, etc. In the illustrated embodiment, the positrons are generated from an X-ray beam 12 projected on patient 11 and interacting with tissues in patient 11. In this case, the apparatus 10 also includes a radiation source 13, such as an accelerator, for generating the X-ray beam 12. This kind of PET is also referred to accelerator based positron emission tomography (A-PET). The X-ray beam 12 may be a pencil-beam, a fan beam, or a cone beam directed from an accelerator.

The positrons travel in patient 11 and collide with electrons therein. Typically, a positron can travel a distance on the order of fraction of millimeter (mm) before colliding with an electron in the tissues in patient 11. In a highly abstract and symbolic way, FIG. 1 shows a positron 51 colliding with an electron 52 in patient 11. Positron 51 and electron 52 annihilate with each other. The annihilation generates a pair of photons, which are symbolically shown in FIG. 1 as a photon 54 and a photon 56. Because of the conservation of momentum, photons 54 and 56 travel in opposite directions from each other in a reference frame coinciding with the center of mass of a two particle system consisting of positron 51 and electron 52 before annihilation. Furthermore, photons 54 and 56 have the same energy as each other.

Apparatus 10 includes a pair of radiation detectors, e.g., a first radiation detector 14 and a second radiation detector 16, positioned on the opposite sides of patient 11. Radiation detectors 14 and 16 detect pairs of photons generated in patient 11 through positron-electron annihilations and generate electrical signals in response to the detected photons. By way of example, U.S. Patent Application Ser. No. 10/013,199 entitled "X-RAY IMAGE ACQUISITION APPARATUS" and filed on Nov. 2, 2001 discloses an X-ray image detecting device that can be used as radiation detector 14 and 16 in accordance with the present invention. U.S. Patent Application Ser. No. 10/013,199 is incorporated herein by reference in its entirety.

Radiation detectors 14 and 16 are coupled to a signal processing module 15. By way of example, U.S. Pat. No. 5,970,115 entitled "MULTIPLE MODE DIGITAL X-RAY IMAGING SYSTEM" and filed on Nov. 25, 1997 and issued on Oct. 19, 1999 discloses a signal process circuit that can be used as signal processing module 15 in accordance with the present invention. U.S. Pat. No. 5,970,115 is incorporated herein by reference in its entirety. The signal detection and processing circuitry disclosed in the above mentioned patents is optimized for integral detection of multiple events per reading. Through the use of specially designed pulse sensitive circuitry, for example, pulse sensitive ASIC modules for amplification, discrimination and rapid timing, large improvements in event sensitivity is available. Multiple channel circuitry designed for optimal single event detection from large amorphous silicon, or other semiconductor material, arrays greatly improves the imaging. In accordance with an embodiment of the present invention, signal processing module 15 includes a signal processor such as, for example, a pulse height analyzer, a pulse coincidence analyzer, a digital signal processor (DSP), a central processing unit (CPU), or a microprocessor (μP), and a memory unit such as, for example, a flash memory, coupled to the signal processor. The signal processor in signal processing module 15 executes various programs stored in the memory unit to process and analyze the electrical signals received from radiation detectors 14 and 16 to generate data regarding the location, path, and energy of the positrons in patient 11 before annihilation. In one embodiment, signal processing module 15 generates image signals of the tissues in patient 11 from the data. The image signals are transmitted to a display 18 coupled to signal processing module 15. The data and the image signals can also be stored in the memory unit in signal process module 15 or stored in an external memory device such as, for example, a hard disk, a floppy disk, a memory tape, a compact disk read only memory (CDROM), a digital video disk (DVD) memory, etc.

It should be noted that the structure and photon detection mechanism of apparatus 10 is not limited to what have been described herein above with reference to FIG. 1. For example, apparatus 10 is not limited to having a pair of radiation detectors 14 and 16 for the detection of photons generated through positron-electron annihilation. In an alternative embodiment of the present invention, apparatus 10 includes a radiation detector having a ring structure surrounding patient 11 for detecting pairs of photon generated through positron-electron annihilation in patient 11. In another alternative embodiment, the pair of radiation detectors 14 and 16 rotate around patient 11 during a PET process to detect electron pairs emitted from patient 11 in different directions. Furthermore, the application of apparatus 10 is not limited to detecting positron-electron annihilation in patient 11. In various aspects of the present invention, apparatus 10 can be used for analyzing the structure of other objects such as, for example, animal bodies, agricultural products, industrial products, mineral products, consumer products. For example, one application of apparatus 10 is detecting diamonds in minerals. Apparatus 10 can also be used for security check in airports, mass transit facilities, buildings, etc.

Figure 2:
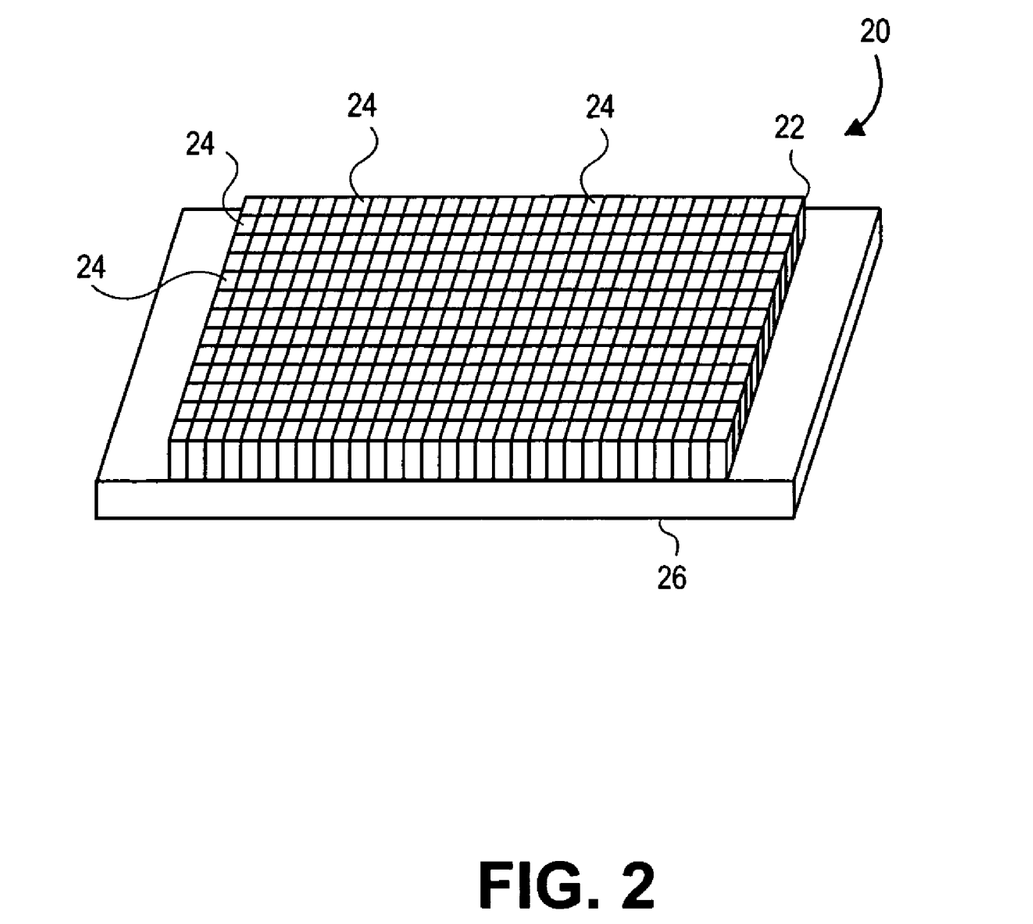
FIG. 2 illustrates a radiation detector in accordance with one embodiment of the present,invention.

FIG. 2 illustrates a radiation detector 20 in accordance with the present invention. Radiation detector 20 can serve as radiation detector 14 and radiation detector 16 in apparatus 10 shown in FIG. 1 in accordance with the present invention. Radiation detector 20 can also have a ring structure instead of the panel structure shown in FIG. 2. Radiation detector 20 includes a photon conversion panel 22 and a photo detector array 26. FIG. 2 shows conversion panel 22 and photo detector array being planar. This is not intended as a limitation on the present invention. For example, conversion panel 22 and photo detector array 26 can also be curved so that radiation detector 20 has a ring structure. Panel 22 includes a plurality of cells 24. In one embodiment, cells 24 are arranged in a two-dimensional array of a plurality of rows and a plurality of columns. Cells 24, which are also referred to as conversion cells, are configured to generate optical light photons in response to X-ray photons generated in the positron-electron annihilation processes, e.g., photons 54 and 56 generated when positron 51 and electron 52 annihilate with each other in patient 11, as symbolically shown in FIG. 1.

Because a positron and an electron each has a mass of $9.1 \times 10^{-34}$ kilograms (kg), the energy for each of the two photon generated during a positron-electron annihilation is at least 0.5 Mega-electron-volts (MeV) due to principle of conservation of energy. Accordingly, conversion cells 24 are preferably sensitive to photons in the 0.5 MeV energy level for positron-electron annihilation detection. For other applications, the conversion cells 24 and associated electronics are preferably configured to detect the type of quanta with appropriate sensitivity. In accordance with one embodiment of the present invention, conversion cells 24 with associated electronics is insensitive to photons having energy less than 0.5 MeV. Thus, a photon not generated in a positron-electron annihilation process and having an energy lower than 0.5 MeV will not generate signals in conversion cells 24.

In accordance with one embodiment, adhesive is used to form conversion panel 22 from conversion cells 24. In accordance with another embodiment, a grid (not shown) is used to arrange conversion cells 24 into the two-dimensional array of X-ray conversion panel 22. Other means can also be used to form the array of X-ray conversion cells 24.

Figure 3:
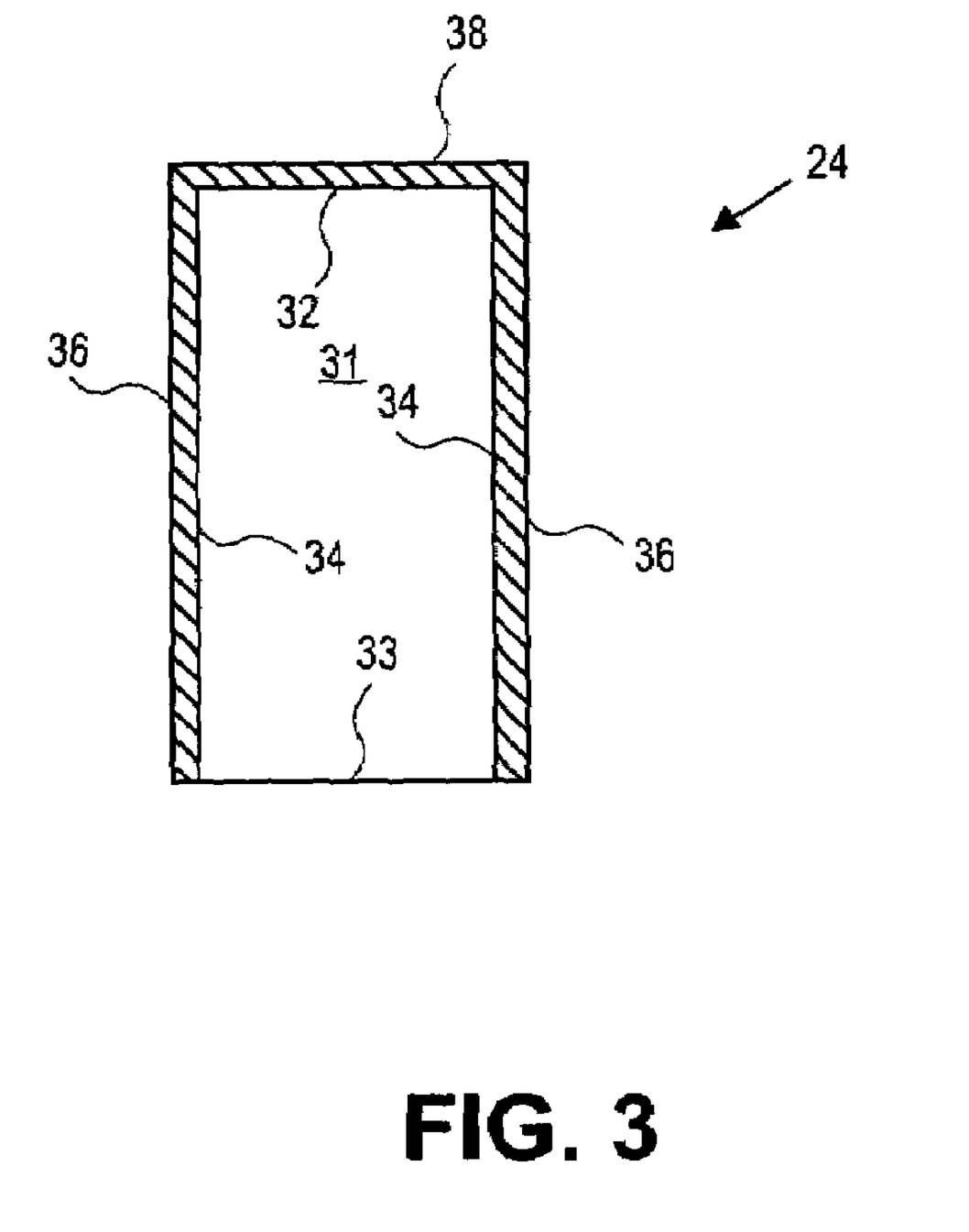
FIG. 3 is a schematic cross sectional view of a conversion cell in accordance with one embodiment of the present invention.

FIG. 3 is a schematic cross sectional view of a conversion cell 24 in conversion panel 22 shown in FIG. 2 in accordance with an embodiment of the present invention. Conversion cell 24 includes an X-ray conversion body 31 having first end 32, a second end 33, and a sidewall 34 extending at least partially between first end 32 and second end 33. In accordance with one embodiment, conversion body 31 is a rod, in which first end 32 and second end 33 are a top and a bottom, respectively, of rod 31. In accordance with the present invention, conversion body 31 is made of a material that generates optical light photons in response to incoming X-ray radiation photons.

In one specific embodiment, conversion body 31 is capable of absorbing the X-ray photons at an energy level of at least 0.5 MeV. In accordance with an embodiment of the present invention, conversion body 31 generates optical light photons having a spectrum ranging between infrared and ultraviolet in response to the X-ray photons. These characteristics are achieved by selecting a suitable material and an appropriate length or height for conversion body 31. In accordance with an embodiment of the present invention, the material has a high X-ray radiation absorption efficiency and is substantially transparent to the optical light photons. Preferred materials for conversion body 31 include Cesium Iodine, Bismuth Germanate, Cadmium Tungstate, etc. Generally, the longer conversion body 31, the more X-ray radiation it can absorb. Preferably, conversion body 31 has an optimum length or height depending on X-ray absorption efficiency, image resolution, light collection efficiency, and other parameters of the radiation detection system design. By way of example, conversion body 31 has a length or height of at least half centimeter. In one embodiment, conversion body 31 has a length or height of approximately one centimeter. Conversion body 31 can also have a length greater than one centimeter. The length or height of conversion body 31 substantially determines the thickness of conversion panel 22 of in radiation detector 20, as shown in FIG. 2.

In one embodiment, first end 32 and second end 33 of conversion body 31 have substantially the same geometric shape and size, and are substantially parallel to each other. In addition, sidewall 34 of conversion body 31 is substantially perpendicular to first end 32 and second end 33. Preferred geometric shapes for first end 32 and second end 33 include square, rectangle, hexagon, etc. The size of first end 32 determines the spatial resolution of the images formed using conversion panel 22. In accordance with an embodiment, first end 32 of conversion body 31 is a square having a side ranging between approximately 0.1 millimeter (mm) and approximately 0.5 mm. In accordance with a specific embodiment, the side of square shaped first end 32 of conversion body 31 is 0.127 mm. In accordance with another specific embodiment, the side of square shaped first end 32 of conversion body 31 is 0.194 mm.

Conversion cell 24 further includes a light reflective film 36 attached to sidewall 34 of conversion body 31. Light reflective film 36 surrounds conversion body 31 and reflects those optical light photons propagating toward sidewall 34 back to the interior of conversion body 31. Therefore, film 36 serves to collimate the optical light photons generated in conversion body 31. In accordance with a specific embodiment, conversion cell 24 also includes an X-ray transparent and optical light reflective film 38 attached to first end 32 of conversion body 31. Film 38 reflects those optical light photons propagating toward first end 32 back toward second end 33 of conversion body 31, thereby increasing the intensity of the light photons reaching photo detector array 26 under conversion panel 22 in radiation detector 20, as shown in FIG. 2. In one embodiment, film 38 on first end 32 of conversion body 31 is a portion of an X-ray transparent and light reflective film covering the entire first end of conversion panel 22. The film covers the first ends of all conversion cells 24 in conversion panel 22. In another embodiment, film 38 is integrally formed with film 36 attached to sidewall 34 of conversion body 31. In this embodiment, film 36 and film 38 form an optical light reflective pocket, in which conversion body 31 is positioned. In yet another embodiment, film 36 for different conversion cells 24 in conversion panel 22 form a grid and conversion cells 24 are positioned in the grid, thereby forming the two-dimensional array of conversion cells in conversion panel 22. Film 36 and film 38 can be made of light reflective materials commercially available. For example, a powder of small grain Magnesium Oxide supported by an appropriate adhesive is a suitable material for light reflective film 36 and film 38. It should be understood that the proper operation of apparatus 10 requires film 38 attached to first end 32 of conversion body 31 to be transparent to the X-ray photons having an energy greater than 0.5 MeV. In one embodiment, film 38 is opaque to photons having energy less than the 0.5 MeV threshold. In such an embodiment, film 38 functions as a filter to screen out photons not generated in positron-electron annihilation and having energy lower the 0.5 MeV threshold. On the other hand, whether film 36 attached to sidewall 34 of conversion body 31 is transparent to the X-ray radiation does not significantly affect the operation of apparatus 10.

Figure 4:
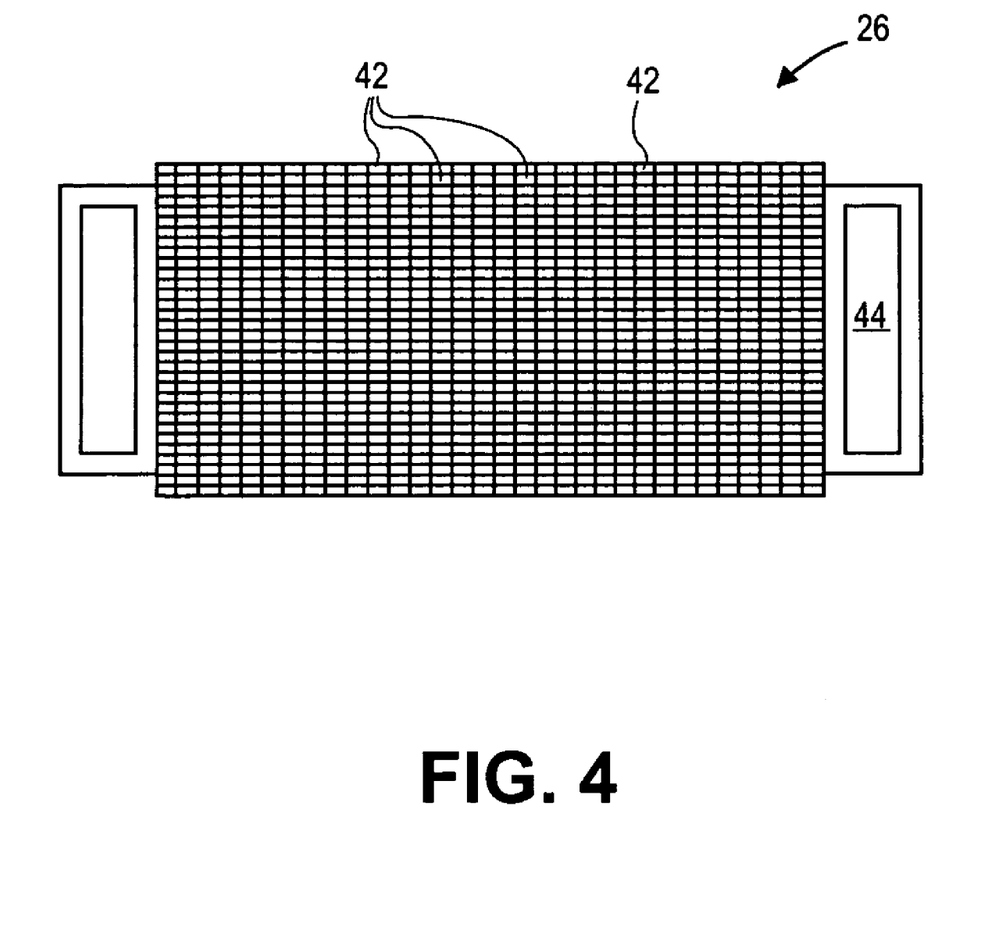
FIG. 4 is a top view of photo detector array in accordance with one embodiment of the present invention.

FIG. 4 is a top view of photo detector array 26 in radiation detector 20 shown in FIG. 2 in accordance with an embodiment of the present invention. Photo detector array 26 includes a plurality of photo detectors 42 arranged in a two-dimensional array. Photo detectors 42 are configured to generate electric signals in response to the optical light photons illuminating thereon. In a specific embodiment, photo detectors 42 are amorphous silicon photo detectors. Each of photo detectors 42 forms a pixel of the image generated using photo detector array 26. Photo detector array 26 also includes a pixel access circuit 44 coupled to photo detectors 42. Pixel access circuit 44 accesses photo detectors 42 and reads the electric signals from photo detectors 42.

In a preferred embodiment, photo detectors 42 in photo detector array 26 are aligned with cells 24 in conversion panel 22. In one embodiment, each conversion cell 24 in conversion panel 22 is aligned with one photo detector 42 in photo detector array 26. In this embodiment, the size of conversion cells 24 is about the same as that of photo detectors 42. The maximum spatial resolution of the images generated using radiation detector 20 is equal to the pixel size of photo detectors 42 in photo detector array 26. In an alternative embodiment, cells 24 in conversion panel 22 are larger than photo detectors 42 in photo detector array 26 and each conversion cell 24 is aligned with more than one photo detectors 42. In this embodiment, the maximum spatial resolution of the images is determined by the size of conversion cells 24.

FIG. 4 shows pixel access circuit 44 located on the side of photo detectors 42. This arrangement keeps pixel access circuit 44 out of the propagation paths of X-ray photons passing through conversion panel 22 and photo detectors 42 and the optical light photons generated in conversion panel 22, thereby benefiting the lifetime of pixel access circuit 44. However, the present invention is not limited to such an arrangement. In an alternative embodiment, photo detectors 42 are mounted on one side of a substrate and pixel access circuit 44 is located on the other side of the substrate. The substrate protects pixel access circuit 44 from possible damage caused by the X-ray photon and optical light photon illumination. This arrangement reduces the physical size of photo detector array 26 without reducing the number of pixels therein.

Pixel access circuit 44 accesses photo detectors 42 in photo detector array 26 and reads the electrical signals therefrom. Compared with a conventional computed tomography (CT) process, the rate at which the X-ray photons striking conversion panel 22 in a PET process is low. Because the photons generated in a positron-electron annihilation process has an energy of at least 0.5 MeV, the electrical signal corresponding to a photon detection event is significantly larger than that of a conventional CT process using a radiation detector similar to radiation detector 20 in a PET process. In order to accurately detect the photons generated in a positron-electron annihilation process, photo detector array 26 is preferably operating in an event sensitive mode as opposed to an integration mode in a conventional CT process. Specifically, pixel access circuit 44 preferably senses each pulse in a pixel 42 in photo detector array 26 in response to a single photon striking radiation detector 20. Operating in the event sensitive mode also improves the signal to noise ratio of pixel accessing circuit 44 compared with the integration mode.

In order to detect the positron-electron annihilation events in patient 11 with a high efficiency, pixel accessing circuit 44 preferably has a accessing rate or signal sensing rate substantially equal to or greater than the photon generation rate through positron-electron annihilation in patient 11. Because of the relatively low photon generation rate in a PET process, e.g., between $10^5$ and $10^7$ photon generations per second, technology for achieving such a signal sensing rate is available. For example, accessing circuits used in bubble chamber and cloud chamber experiments in nuclear or elementary particle physics laboratories generally have accessing rates sufficiently high for applications in accordance with the present invention.

In accordance with one embodiment, pixel accessing circuit 44 has a predetermined pixel accessing rate, e.g., between one access and ten access every microsecond (µs). The electrical charge generated in a particular photo detector 42 in response to an optical light photon is stored in a capacitor in corresponding photo detector 42 until it is read out by pixel accessing circuit 44 in a subsequent pixel access action. In another embodiment, an electrical signal is read out from a particular photo detector 42 at the time of its occurrence in response to an optical light photon striking corresponding photo detector 42. This real time read out or signal sensing process provides superior temporal resolution capabilities for detecting pairs of photons generated in the positron-electron annihilation.

Figure 5:
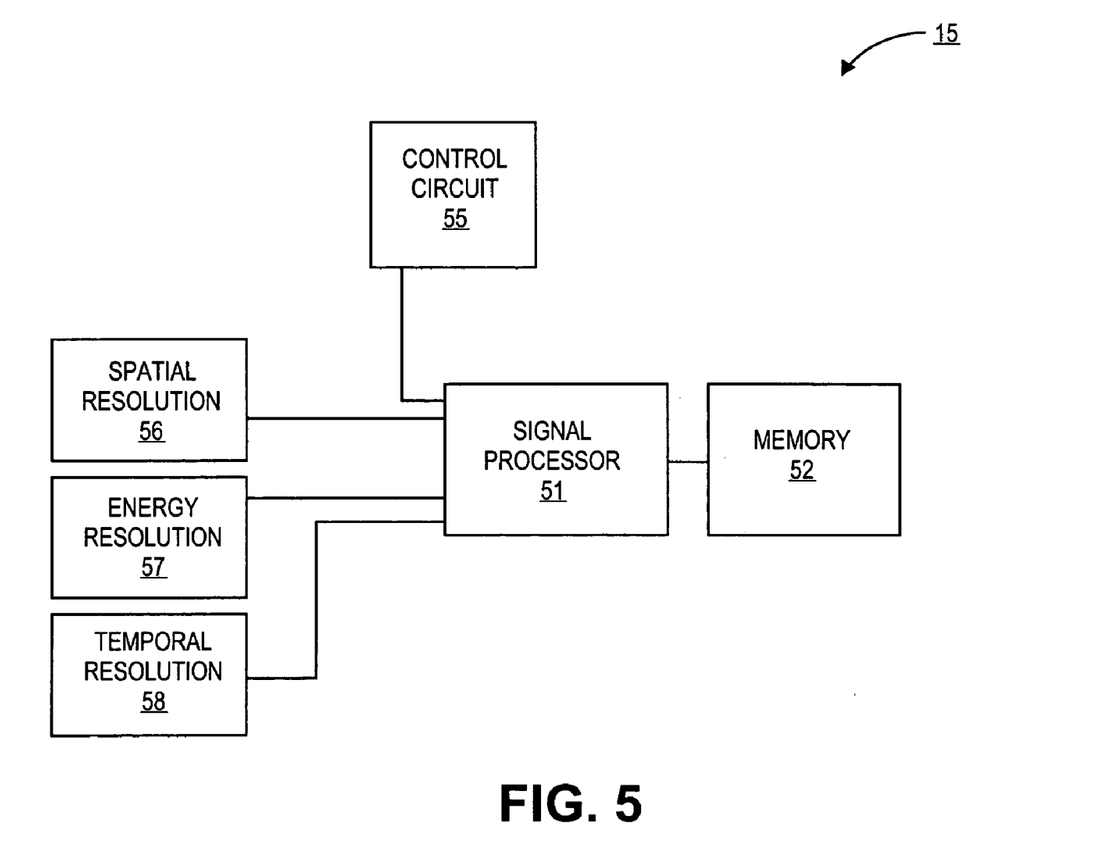
FIG. 5 is a block diagram schematically illustrating a functional structure of signal processing module in accordance with one embodiment of the present invention.

FIG. 5 is a block diagram schematically illustrating a functional structure of signal processing module 15. As described herein above with reference to FIG. 1, signal processing module 15 includes a signal processor 51 and a memory unit 52 coupled to signal processor 51. In addition, signal processing module 15 includes a control circuit 55 coupled to signal processor 51. Control circuit 55 can be a microcontroller, an application specific integrated circuit (ASIC), etc. Control circuit 55 controls the operation of pixel access circuit 44 in photo detector array 26.

In one aspect of the present invention, the positrons are generated by X-ray pulses projected onto patient 11 in an A-PET process. The X-ray pulse width and rate are determined by the accelerator pulse width and rate. By way of example, the X-ray pulses may have a rate between approximately 100 pulses per second (Hz) and approximately 1000 Hz, with each pulse having a pulse width between approximately 0.5 µs and approximately 100 µs. In such an A-PET process, control circuit 55 can so control pixel access circuit 44 that it senses and reads signals from photo detectors 42 only during the periods when X-ray pulses are on. In accordance with an embodiment, control circuit 55 synchronizes the signal sensing period of pixel accessing circuit 44 with the X-ray pulses generated by the accelerator. Sensing the signal only during the pulse-on periods eliminates false signals during the pulse-down periods and improves the signal to noise ratio of radiation detector 20.

In accordance with various specific embodiments of the present invention, control circuit 55 further commands pixel accessing circuit 44 to reset photo detectors 42 during the pulse-down periods. In one such specific embodiment, pixel accessing circuit 44 resets all photo detectors 42 in photo detector array 26, regardless of whether a particular photo detector 42 detected a photon in the previous pulse-on period. In another such specific embodiment, pixel accessing circuit 44 resets a particular photo detector 42 in photo detector array 26 only if that photo detector 42 detected a photon in the previous pulse-on period.

In another aspect of the present invention, the positrons are generated through the decay of radioactive isotopes administrated to patient 11. In such a PET process, control circuit 55 can control pixel access circuit 44 to sense and read signals from photo detectors 42 in continuous sensing process, either at a predetermined rate or on a real time basis as described herein above. Control circuit 55 further commands pixel accessing circuit 44 to reset photo detector 42 after sensing the signals therefrom. In one embodiment, pixel accessing circuit 44 resets all or part of photo detectors 42 in photo detector array 26 at a predetermined rate, e.g., at the same rate as the predetermined signal sensing rate. In another embodiment, pixel accessing circuit 44 resets a particular photo detectors 42 after reading signals therefrom.

Signal processing module 15 also includes a spatial resolution circuit 56, a photon energy resolution circuit 57, and a temporal resolution circuit 58, all which are coupled to signal processor 51. Spatial resolution circuit 56 calculates the paths of incoming photons from which pixels the pair of photons strike. Photon energy resolution circuit 57 calculates the energy of the photons from the intensity of the signals generated in photo detectors 42. Temporal resolution circuit 58 calculates the time difference between two photon striking events. Two photons generated in the same positron-electron annihilation process travel in opposite directions from each other, have substantially the same energy, and are generated substantially at the same time. Data regarding the paths, energy, and time of the photons can be used to determine whether the two photons are generated in the same positron-electron annihilation and determine where and when the positron-electron annihilation takes place. The data can also be used to determine the location and velocity of the positron immediately before the annihilation. Because a positron has a very short life time in patient 11, it typically travels less than one millimeter before colliding and annihilating with an electron in patient 11. Accordingly, the location and time of positron generation in patient 11 can be derived from the data. Signal processor 51 can further derive the positron density distribution in patient 11 and generate images of various tissues in patient 11.

The images generated through event sensitive radiation detector 20 and signal processing module 15 are not limited to cross sectional tomographical images of patient 11. In accordance with the present invention, apparatus 10 with event sensitive radiation detector 20 can generate other types of images using positron density distribution data, which include images in a volume, images in multiple planes, images along a single line, multiple lines, or arbitrarily shaped conical surfaces in patient 11.

It should noted that FIG. 5 illustrates only the functional structure of signal processing module 15. It is not intended to place any limitation on the physical structure or circuit schematics of signal processing module 15. For example, spatial resolution circuit 56, energy resolution circuit 57, and temporal resolution circuit 58 are not limited to being three circuit blocks separate from each other. They can belong to one circuit block. They can also be part of signal processor 51.

The application of apparatus 10 in accordance with the present invention is not limited to PET. Specifically, radiation detector 20 is not limited to detecting photons generated in positron-electron annihilations. Radiation detector 20 is event sensitive in accordance with the present invention and can detect photons generated in other processes such as, for example, Compton scattering, photoelectric effect, single photon emission, pair photon production, etc. Furthermore, event sensitive radiation detector 20 can be modified to detect other radiation, which include both neutral and charged particles, e.g., neutrons, electrons, protons, positrons, etc. In accordance with the present invention, radiation detector 20 and its variations are applicable in various kinds of processes in which occurrence of events, not the accumulative effects of the events, is measured and analyzed. Because different radiation have different energy spectra and different cross sections, modifications to the composition and structure of conversion panel 22 in front of amorphous silicon photo detector array 26 may be advantageous in achieving preferred characters and performance of radiation detector 20 such as, for example, sensitivity, signal to noise ratio, threshold energy, spatial resolution, energy resolution, temporal resolution, etc.

Event sensitive radiation detector 20 can be used with different radiation sources to generate different images. In one example, an X-ray source having a laminar collimator can perform a pencil beam raster scan on patient 11 to generate accelerator based single photon emission computed tomography (A-SPECT) images with higher spatial resolution and lower radiation exposure to patient 11 compared with conventional CT. In this case, a collimator may be placed adjacent to the radiation detector 20 to thereby allow the radiation detector 20 to detect radiation particles traveling in a certain direction. Based on a direction of travel of the particle and a position on the detector 20 where the particle is detected, the origin of the particle may be determined. In another example, event sensitive radiation detector 20 is able to detect and identify two types of events: single photon Compton scattering and positron-electron annihilation. Single photon Compton scattering and positron-electron annihilation are distinguishable from each other because each Compton scattering event generates a single photon and positron-electron annihilation generates photons in pairs. Furthermore, the two processes generate photons with different characteristics such as, for example, different energy spectra and different trajectories. Signal processing module 15 processes the signals for both Compton scattering detection and positron-electron annihilation detection to generate tomographical images of patient 11. Because Compton scattering takes place in patient 11 independent of positron generation and positron-electron annihilation, generating Compton scattering and A-PET images does not require the increase of the total radiation exposure of patient 11.

In accordance with various aspects of the present invention, applications of apparatus 10 and its variations include, but are not limited to, structural and/or functional analysis of other objects such as, for example, animal bodies, agricultural products, industrial products, mineral products, consumer products, luggage/cargo in airport, mass transit facility, and building security check, etc. For example, one application of apparatus 10 is analyzing the composition of minerals. Different compositions typically have different characters such as, for example, different densities, different atomic numbers, etc. These different characters result in different cross section areas for positron-electron pair production, positron-electron annihilations and Compton Scattering. For example, the cross section area of positron-electron pair production is proportional to $$\sum_i N_i Z_i^2,$$

wherein $Z_i$ is the atomic number of an element in a composition in the mineral and $N_i$ is the number of atoms of the element in the composition. Different cross section areas give rise to different positron-electron annihilation and Compton scattering rates. Radiation detectors 14 and 16 in apparatus 10 sense the different positron-electron annihilation and/or Compton Scattering rates and generate signals in response thereto. Signal processing module 15 processes the signals to generate data and images regarding the compositions and structures of the minerals.

Figure 6:
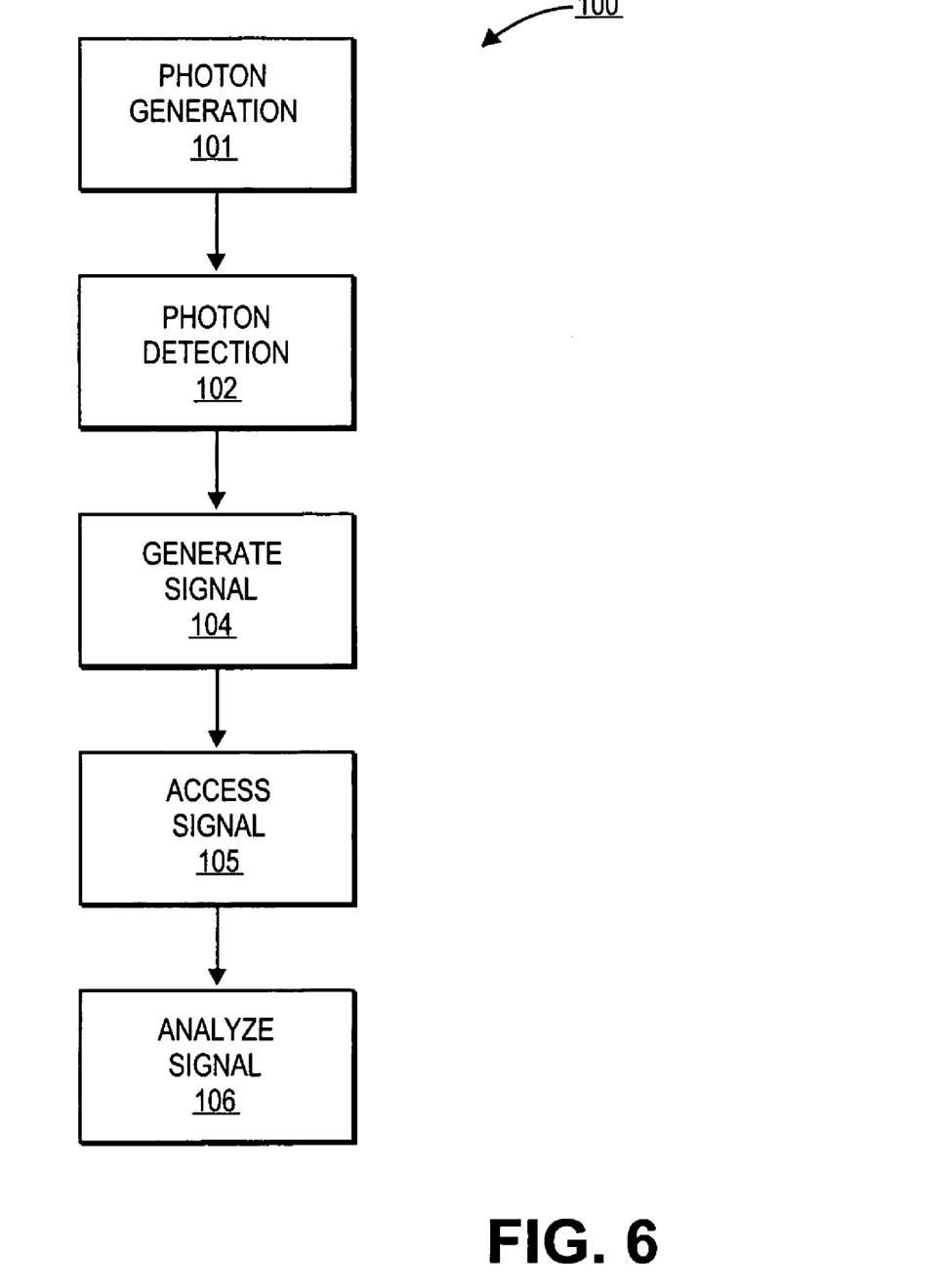
FIG. 6 is a flow chart schematically illustrating a process for inspecting an object in accordance with one embodiment of the present invention.

FIG. 6 is a flow chart schematically illustrating a process 100 for inspecting an object in accordance with the present invention. In one example, the object is a patient and process 100 performs a PET or a SPECT on the patient. In another example, the object is a piece of luggage or cargo going through a security check and process 100 inspects the object for contrabands or explosives. In yet another example, the object is a piece of mineral rock and process 100 inspects the rock for specific composition such as, for example, diamond.

In accordance with the present invention, process 100 of inspecting the object starts with a step 101 of introducing a photon generation mechanism into the object to generate a photon. In accordance with one embodiment, the photon generation mechanism includes a positron generating isotope administrated to the object. The positrons generated from the isotope collide with particles in the object, which result in positron-electron annihilation or Compton scattering. In accordance with another embodiment, an X-ray radiation generates positrons, which inter generate the photons in a positron-electron annihilation process. In accordance with yet another embodiment, the X-ray radiation excites the particles in the object to generate the photons directly.

In a step 102 of inspection process 100, the photons generated in the object are detected as they transmit out of the object. In a step 104, process 100 generates an electrical signal in response to a photon detection event. In a step 105, the electrical signal is accessed using an accessing circuit. In accordance with an embodiment of the present invention, the accessing circuit operates in an event sensitive mode to access the electrical signal corresponding to each photon detection event. The accessed signal is analyzed in a step 106 to generate the data regarding the internal structure of the object. The data may be used to generating tomographic images of the object or detect specific composition of the object. In accordance with various embodiments of the present invention, analyzing the electric signal may include identifying a spatial coordinate of the photon, identifying a time of generation of the photon, identifying an energy. of the photon, or any combination thereof.

By now it should be appreciated that an apparatus and a method for inspecting an object with event sensitive photon detection have been provided. In accordance with the present invention, the apparatus includes an accessing circuit and a signal processing module operating in an event sensitive mode that is capable of detecting single photon events. In an aspect of the present invention, the apparatus detects photons in a PET or a SPECT process. Specifically, the PET process or the SPECT process with event sensitive photon detection in accordance with the present invention provides accurate imaging data without the need for increasing radiation exposure of the object. The electronic circuitry for event sensitive photon detection has significantly lower intrinsic noise compared with the circuitry operating in integration signal accessing mode used in conventional computed tomography. Therefore, the imaging apparatus with event sensitive photon detection in accordance with the present invention is able to minimize the possible adverse side effect of a PET or SPECT process. Furthermore, the event sensitive photon detection improves the efficiency and reduces the operating cost of the PET or SPECT process.

While specific embodiments of the present invention have been described herein above, they are not intended as a limitation on the scope of the present invention. The present invention encompasses those modifications and variations of the described embodiments obvious to those skilled in the art.

What is claimed is:

1. A method for examining an object, comprising:
    directing an externally generated radiation beam towards an object to generate a positron-electron annihilation process to produce photons in the object;
    detecting the photons;
    generating a signal in response to the detected photons; and
    determining a characteristic of the object based at least on the signal.

2. The method of claim 1, wherein the object comprises at least a portion of an animal body.

3. The method of claim 1, wherein the object comprises a non-animal object.

4. The method of claim 1, wherein the object comprises a passenger, a luggage or a cargo, and the determining a characteristic of the object comprises determining whether the object contains contraband or explosive.

5. The method of claim 1, wherein the object comprises a mineral rock, and the determining a characteristic of the object comprises determining whether the object contains a diamond.

6. The method of claim 1, wherein the determining comprises generating data regarding the object.

7. The method of claim 6, wherein the data comprises image data.

8. The method of claim 6, wherein the data comprises PET or SPECT data.

9. The method of claim 1, wherein the characteristic of the object comprises a composition, an electron density, an atomic number density, a mass density, a morphology, an appearance, or a functionality.

10. The method of claim 1, wherein the directing the externally generated beam comprises directing a pencil-beam, a fan beam, or a cone beam towards the object.

11. The method of claim 1, further comprising accessing the signal as the signal is generated and before the signal integrates with another signal.

12. The method of claim 1, wherein the determining comprises identifying one or a combination of a spatial coordinate, a time of generation, and an energy of the detected photons.

13. The method of claim 1, wherein the detecting the photons comprises using a first detector to sense a first photon generated in a positron-electron annihilation process, and using a second detector to sense a second photon generated in the positron-electron annihilation process.

14. The method of claim 13, wherein the determining a characteristic of the object comprises determining whether the first photon and the second photon both originated from the same positron-electron annihilation process based at least on a time when the first photon is detected in the first detector and a time when the second photon is detected in the second detector.

15. The method of claim 13, wherein the determining a characteristic of the object comprises determining an energy level associated with the first photon and an energy level associated with the second photon.

16. The method of claim 15, wherein the determining an energy level further comprises considering only signals associated with an energy level that is approximately 0.5 MeV or higher.

17. The method of claim 13, wherein the determining a characteristic of the object further comprises determining an origin of the first and second photons where the positron-electron electron annihilation process occurred.

18. The method of claim 1, wherein:
the step of directing an externally generated radiation beam comprises using a radiation source;
the step of detecting the photons comprises using a first detector and a second detector; and
the radiation source is not located between the first and the second detectors.

19. A system for examining an object, comprising:
means for externally generating a radiation beam and directing the radiation beam towards an object to generate a positron-electron annihilation process to produce photons in the object;
means for detecting the photons;
means for generating a signal in response to the detected photons; and
means for determining a characteristic of the object based at least on the signal.

20. The system of claim 19, wherein the means for externally generating the radiation beam comprises means for generating a pencil-beam, a fan beam, or a cone beam.

21. The system of claim 19, further comprising means for accessing the signal as the signal is generated and before the signal integrates with another signal.

22. The system of claim 19, wherein the means for determining a characteristic of the object comprises means for generating data regarding the object.

23. The system of claim 19, wherein the means for detecting the photons comprises a first detector and a second detector, and the means for externally generating the radiation beam is not located between the first and the second detectors.

24. A method for examining an object, comprising:
generating a particle in an object;
detecting the particle;
generating a signal using a detector in response to the detected particle;
accessing the generated signal using an accessing circuit that has an accessing rate equal to or greater than a signal generating rate associated with the detector; and
analyzing the signal to generate data regarding the object.

25. The method of claim 24, wherein the generating a particle comprises directing a beam towards the object.

26. The method of claim 25, wherein the directing a beam comprises directing a pencil-beam, a fan beam, or a cone beam towards the object.

27. The method of claim 24, wherein the generating a particle comprises introducing a radioactive isotope into the object.

28. The method of claim 24, wherein the particle comprises a photon generated in a positron-electron annihilation process.

29. The method of claim 24, wherein the particle comprises a proton, a positron, a neutron, or an electron.

30. The method of claim 24, wherein the analyzing comprises identifying one or a combination of a spatial coordinate, a time of generation, and an energy of the detected particle.

31. The method of claim 24, wherein the object comprises at least a portion of a body of a patient undergoing a positron emission tomography (PET) scanning or a single-photon emission computed tomography (SPECT) scanning.

32. The method of claim 24, wherein the object comprises a passenger, a luggage or a cargo, and the process further comprising determining whether the object contains contraband or explosive based at least on the generated data.

33. The method of claim 24, wherein the object comprises a mineral rock, and the process further comprising determining whether the object contains a diamond.

34. The method of claim 24, wherein the signal generating rate is associated with a rate at which particles are detected.

35. A system for examining an object, comprising:
means for generating a particle in an object;
means for detecting the particle;
means for generating a signal in response to the detected particle;
an accessing circuit for accessing the generated signal the accessing circuit having an accessing rate ectual to or greater than a signal generating rate associated with the means for generating; and
means for analyzing the signal to generate data regarding the object.

36. The system of claim 35, wherein the means for generating a particle comprises means for directing a beam towards the object.

37. The system of claim 35, wherein the means for generating a particle comprises means for introducing a radioactive isotope into the object.

38. The system of claim 35, wherein the particle comprises a photon generated in a positron-electron annihilation process.

39. The system of claim 35, wherein the particle comprises a proton, a positron, a neutron, or an electron.

40. The system of claim 35, wherein the means for analyzing comprises means for identifying one or a combination of a spatial coordinate, a time of generation, and an energy of the detected particle.

41. The system of claim 35, wherein the signal generating rate is associated with a rate at which particles are detected by the means for detecting.

42. An imaging apparatus, comprising:
a conversion panel configured to generate a light photon in response to a radiation;

a photo detector array aligned with the conversion panel and configured to generate a signal in response to the light photon received from the conversion panel;

an access circuit coupled to the photo detector array, the accessing circuit having accessing rate equal to or greater than a signal generating rate associated with the photo detector; and a signal processing circuit coupled to the access circuit and configured to generate image data in response to the signal received by the access circuit.

43. The apparatus of claim 42, wherein the photo detector array having a plurality of amorphous silicon photo detectors arranged in a two dimensional array.

44. The apparatus of claim 42, wherein the access circuit being configured to read signals generated in the photo detector array at a rate between approximately $10^4$ and $10^8$ times per second.

45. The apparatus of claim 42, wherein the access circuit being further configured to reset the photo detector array after reading one or more signals therefrom.

46. The apparatus of claim 42, further comprising
an additional conversion panel positioned adjacent to the conversion panel, the additional conversion panel configured to generate a light photon in response to a radiation; and
an additional photo detector array aligned with the additional conversion panel, the additional photo detector array coupled to the access circuit and is configured to generate a signal in response to the light photon received from the additional conversion panel.

47. The apparatus of claim 46, wherein the signal processing circuit being further configured to determine whether a radiation detected at the conversion panel is associated with a radiation detected at the additional conversion panel based at least on a position of a radiation source relative to the conversional panel and the additional conversional panel.

48. The apparatus of claim 46, wherein the signal processing circuit being configured to determine whether a radiation detected at the conversion panel is associated with a radiation detected at the additional conversion panel based at least on an energy level of a radiation detected at the conversion panel and an energy level of a radiation detected at the additional conversion panel.

49. The apparatus of claim 46, wherein the signal processing circuit being configured to determine whether a radiation detected at the conversion panel is associated with a radiation detected at the additional conversion panel based at least on a position of a first particle detected at the conversion panel and a position of a second particle detected at the additional conversion panel.

50. The apparatus of claim 42, further comprising an accelerator configured to direct a radiation beam onto an object to generate the radiation.

51. The apparatus of claim 42, further comprising a platform for supporting an object.

52. The apparatus of claim 42, wherein the signal generating rate is associated with a rate at which photons are received by the conversion panel. for supporting an object.

* * * * *